United States Patent
Chen et al.

(10) Patent No.: US 6,649,043 B1
(45) Date of Patent: *Nov. 18, 2003

(54) REGENERATION OF HYDROGEN SULFIDE SORBENTS

(75) Inventors: Jingguang G. Chen, Hockessin, DE (US); Leo D. Brown, Baton Rouge, LA (US); William C. Baird, Jr., Baton Rouge, LA (US); Gary B. McVicker, Califon, NJ (US); Edward S. Ellis, Fairfax, VA (US); Michele S. Touvelle, Baton Rouge, LA (US); Darryl P. Klein, Ellicott City, MD (US); David E. W. Vaughan, Flemington, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 350 days.

This patent is subject to a terminal disclaimer.

(21) Appl. No.: 09/620,865

(22) Filed: Jul. 21, 2000

Related U.S. Application Data

(63) Continuation-in-part of application No. 09/326,827, filed on Jun. 7, 1999, now Pat. No. 6,221,240, which is a continuation-in-part of application No. 08/918,641, filed on Aug. 22, 1997, now Pat. No. 5,935,420.
(60) Provisional application No. 60/024,737, filed on Aug. 23, 1996.

(51) Int. Cl.$^7$ .................. C10G 45/00; C10G 25/00; C10G 25/12
(52) U.S. Cl. .................. 208/213; 208/217; 585/826; 502/34; 502/38; 502/53
(58) Field of Search .................. 208/213, 217; 585/826; 502/34, 38, 53

(56) References Cited

U.S. PATENT DOCUMENTS

| | | | |
|---|---|---|---|
| 2,983,669 A | 5/1961 | Noll | 208/97 |
| 3,539,306 A | 11/1970 | Kumura et al. | 23/315 |
| 3,796,792 A | 3/1974 | Miyata et al. | 423/250 |
| 3,879,523 A | 4/1975 | Miyata et al. | 423/250 |
| 4,263,020 A | 4/1981 | Eberly | 55/62 |
| 4,371,507 A * | 2/1983 | Farha, Jr. et al. | 423/230 |
| 4,454,244 A | 6/1984 | Woltermann | 502/208 |
| 4,455,286 A * | 6/1984 | Young et al. | 423/230 |
| 4,690,806 A * | 9/1987 | Schorfheide | 423/230 |
| 4,831,206 A | 5/1989 | Zarchy | 585/737 |
| 4,831,207 A | 5/1989 | O'Keefe et al. | 585/737 |
| 4,990,242 A | 2/1991 | Louie et al. | 208/218 |
| 5,057,296 A | 10/1991 | Beck | 423/277 |
| 5,185,135 A | 2/1993 | Pillai et al. | 423/320 |
| 5,283,047 A | 2/1994 | Vaughan et al. | 423/713 |
| 5,366,614 A | 11/1994 | Russ et al. | 208/65 |
| 5,439,583 A | 8/1995 | Robinson et al. | 208/62 |
| 5,518,607 A | 5/1996 | Field et al. | 208/212 |
| 5,891,323 A * | 4/1999 | Willis | 208/211 |
| 5,925,239 A | 7/1999 | Klein et al. | 208/213 |
| 5,928,498 A * | 7/1999 | McVicker et al. | 208/213 |
| 5,935,420 A * | 8/1999 | Baird, Jr. et al. | 208/213 |
| 5,985,136 A | 11/1999 | Brignac et al. | 208/216 R |
| 6,007,704 A | 12/1999 | Chapus et al. | 208/218 |
| 6,103,106 A | 8/2000 | McVicker et al. | 208/213 |
| 6,221,240 B1 * | 4/2001 | Klein et al. | 208/213 |
| 6,245,221 B1 * | 6/2001 | Baird, Jr. et al. | 208/213 |
| 6,334,948 B1 | 1/2002 | Didillon et al. | 208/218 |

OTHER PUBLICATIONS

Hydrodesulfurization of Methyl–Substituted Dibenzothophenes Catalyzed by Sulfided Co–Mo / y–Al2O3, M. Houalla et al., Journal of Catalysis, 61, (1980), 523–527.—No month.

Reactives, Reaction Networks, and Kinetics in High–Pressure Catalytic Hydroprocessing, Girgis and Gates, Ind. Eng. Chem, 30, (1991), 2021–2058.—No month.

Hydrotalcite–Type Anionic clays: Preparation, Properties and Applications, Cavani et al., Catalysis Today, vol. 11, No. 2, (1991), 173–301.—No month.

A Review of Deep Hydrodesulfurization Catalysis, Vasudevan et al., Catalysis Reviews—Sci. Eng., 38, (2) (1996), 161–188.—No month.

Deep hydrodesulfurization of diesel fuel: Design of reaction process and catalysis, Mochida et al., Catalysis Today 29 (1996), 185–189.—No month.

Effect of experimental parameters on the relative reactivity of dibenzothiophene and 4–methyldibenzothiophene, Lamure–Meille et al., Applied Catalysis A: General 131 (1995), 143–157.—No month.

* cited by examiner

*Primary Examiner*—Nadine G. Norton
(74) *Attorney, Agent, or Firm*—Gerard J. Hughes

(57) ABSTRACT

A process to regenerate metal oxide desulfurization sorbents using an oxidizing and reducing atmosphere. The sorbents may be mono- or multi-metallic in nature, and preferably comprise Cu, Ni and/or Co. If desired, secondary metals may be incorporated to increase regeneration efficiency and/or capacity. Other additives may be used to suppress hydrocarbon cracking. A sorbent containing Zn may be combined with an Fe, Co, Ni, Mo, or W catalyst or a noble metal catalyst and combinations thereof.

31 Claims, No Drawings

REGENERATION OF HYDROGEN SULFIDE SORBENTS

CROSS REFERENCE TO RELATED APPLICATIONS

The present application is a continuation-in-part of U.S. Ser. No. 09/326,827, filed Jun. 7, 1999, now U.S. Pat. No. 6,221,240 which is a continuation-in-part of U.S. Ser. No. 08/918,641, filed Aug. 22, 1997, issued Aug. 10, 1999 as U.S. Pat. No. 5,935,420, which claims the benefit of Provisional Application Ser. No. 60/024,737 filed Aug. 23, 1996.

FIELD OF THE INVENTION

The invention relates to methods for regenerating metal and metal oxide hydrogen sulfide sorbents by treating the spent sorbents with an oxidizing atmosphere following by a reducing atmosphere. The sorbents may be mono- or multi-metallic in nature.

BACKGROUND OF THE INVENTION

The removal of sulfur from feedstocks is a fundamental process of the refining and petrochemical industries. One process for removing sulfur from a feedstock is hydrodesulftirization. Hydrodesulfurization involves the reaction of sulfur in the feedstock with hydrogen over noble metals, such as Pt, Pd, or non-noble metal sulfides, especially Co/Mo and Ni/Mo catalysts, at fairly severe temperatures and pressures to form hydrogen sulfide. The performance of the hydrodesulfurization catalysts can be inhibited by the presence of hydrogen sulfide. The use of sorbents to remove the hydrogen sulfide produced during the reaction improves the effectiveness of the overall hydrodesulfurization process.

The performance of a hydrogen sulfide sorbent depends on a variety of properties. Thermodynamics and kinetics of sulfidation clearly are important, because they determine the overall sulfur capacity before breakthrough at some predetermined level of $H_2S$. Other important sorbent properties include stability and regenerability in extended use, the operating conditions required for regeneration, and the composition of the regeneration off-gas, which largely determines the choice of a downstream sulfur recovery process.

A practical limitation on the use of any hydrogen sulfide sorbent is the ability to regenerate the sorbent. The scope and applicability of such sorbents is limited by economic constraints relating to the level of sulfur being processed, the reactor volumetrics required, and issues pertaining to removal and disposal of the spent sorbent. These limitations are relieved if the sulfur sorbent is capable of multicycle operation made possible by a means for regenerating the sorbent material.

SUMMARY OF THE INVENTION

The present invention provides a process for regenerating a hydrogen sulfide sorbent comprising providing a spent hydrogen sulfide sorbent containing metal or metal oxide wherein the metal is at least one of Fe, Ni, Cu, Co, and Zn. Fresh hydrogen sulfide sorbent may be characterized by a level of sulfur defining a first cycle capacity for absorbing hydrogen sulfide. The spent hydrogen sulfide sorbent may be regenerated by first exposing it to a gas comprising a regenerating concentration of an oxidizing gas under conditions effective to oxidize said spent hydrogen sulfide sorbent. The oxidized hydrogen sulfide sorbent is then exposed to a gas comprising a regenerating concentration of a reducing gas under conditions effective for the gas to regenerate the spent hydrogen sulfide sorbent, thereby producing a regenerated sorbent having an effective regenerated capacity for sulfur.

DETAILED DESCRIPTION OF THE INVENTION

The present invention uses a combination of an oxidizing atmosphere and a reducing atmosphere to regenerate solid sorbents. The oxidizing atmosphere may comprise any gas capable of oxidizing the spent sorbent, including but not necessarily limited to oxygen and oxygen blends. The oxidizing atmosphere may also contain, for example, steam, carbon dioxide, and inert diluents such as light hydrocarbons, nitrogen, and helium. An oxygen-containing gas is the most preferred oxidizing gas. The reducing atmosphere may comprise any gas capable of reducing the sorbent, including but not necessarily limited to hydrogen, carbon monoxide, and blends thereof. Hydrogen is preferred. The reducing gas may also contain steam and inert gases such as nitrogen, helium, and light hydrocarbons.

In one embodiment, a spent sorbent is exposed to a gas comprising a regenerating concentration of an oxidizing gas under conditions effective to oxidize the spent sorbent to its corresponding sulfite or sulfate. Further decomposition to $SO_X$ species may also occur. In a preferred embodiment, the oxidized products are exposed to an inert purge. Following the optional purge, the oxidized products are then exposed to a gas comprising a regenerating concentration of a reducing gas under conditions effective to regenerate the oxidized spent hydrogen sulfide sorbent in order to convert the oxidized products to the corresponding metal or reduced oxide, which regenerates the sorbent to an active state, producing a regenerated sorbent having an effective regenerated capacity.

The regenerable sorbents of the present invention comprise at least one metal or oxide of the metal, the metal(s) being selected from Fe, Ni, Co, Ag, Sn Re, Mo, Cu, Pt, Pd and Zn. In a preferred embodiment, the metal is at least one of Fe, Ni, Co, Cu, and Zn. The sorbent may be supported on an inorganic support material in order to, for example, increase surface area, pore volume, and pore diameter. Suitable support materials contain at least one inorganic refractory support materials including, but not necessarily limited to, alumina, silica, zirconia, carbon, silicon carbide, kieselguhr, amorphous and crystalline silica-aluminas, silica-magnesias, aluminophosphates, boria, titania, and zinc oxide. Preferred support materials include alumina, zirconia, and silica. The metal(s) or metal oxide(s) may be loaded onto these supports by conventional techniques known in the art. Non-limiting examples of suitable supported metal and metal oxide based regenerable sulfur sorbents include, but are not necessarily limited to: $Co/Al_2O_3$; $Co/SiO_2$; $Co/TiO_2$; $Co/ZrO_2$; $Ni/Al_2O_3$; $Ni/SiO_2$; $Ni/ZrO_2$; $Cu/Al_2O_3$; $CU/SiO_2$; $Cu/ZrO_2$; $Fe/Al_2O_3$; $Fe/SiO_2$; $Fe/ZrO_2$; $Co/Cu/Al_2O_3$; $Co/Cu/SiO_2$; $Ni/Cu/SiO_2$; $Ni/Cu/ZrO_2$; $Co/Pt/Al_2O_3$; $Co/Pd/SiO_2$; $Co/Sn/Al2O_3$; $Ni/Sn/SiO_2$; $Zn/Al2O_3$, $ZnO/SiO_2$, $Co/ZnO$; $Mo/ZnO$; $Ni/ZnO$; $Co/Mo/ZnO$; $Ni/Mo/ZnO$; $Pt/ZnO$; $Pd/ZnO$; $Pt/Pd/ZnO$. The sorbent may also be employed as a bulk metal oxide or as a bulk metal, including but not necessarily limited to, a finely divided skeleton metal, including Raney metals, ponderous metals, Rieke metals, and metal sponges.

Such techniques include impregnation by incipient wetness, adsorption from excess impregnating medium, and ion exchange. In a preferred embodiment, the regenerable sorbents are prepared by conventional impregnation techniques using aqueous solutions of metal halides, oxides, hydroxides, carbonates, nitrates, nitrites, sulfates, sulfites, carboxylates and the like. The metal or metal oxide loadings may vary with the quantity of sulfur to be adsorbed per cycle, the cycle frequency, and the regeneration process conditions and hardware. Metal loadings of from about 2 wt. % to about 80 wt. % are preferred, from about 3 wt. % to about 60 wt. % are more preferred, and from about 5 wt. % to about 50 wt. % are most preferred.

After impregnation onto a support, the sorbent typically is dried, calcined, and reduced; the latter either may be conducted ex situ or in situ, as preferred. The regenerable hydrogen sulfur sorbent may comprise a single metal or two or more metals. Certain metal combinations offer improved capacity, regenerability, and operability over the use of the individual metals. For bi- and polymetallic sorbents, similar ranges apply to each component; however, the loading may be either balanced or unbalanced, with the loading of one metal being greater than or less than the other.

Some sorbents, particularly those containing Fe, Co, and Ni, may be active for hydrocracking. If desired, the hydrocracking activity may be suppressed by incorporating at least one hydrocracking suppressor selected from one or more of the Group IB, Group IVA, and Group VIA elements of the Periodic Table. The Periodic Table of the Elements used herein appears on the inside front cover of the Merck Index, Twelfth Edition, Merck & Co., 1996. When the hydrocracking suppressor is selected from Group IB and Group IVA elements, it is preferably at least one of Cu, Ag, Au, Sn, and Pb, and may be present in an amount ranging from about 1 wt. % to about 10 wt. %, preferably from about 2 wt. % to about 6 wt. %, based on the weight of the sorbent. The most preferred element is Cu. When the hydrocracking suppressor is at least one Group VIA element, then it may be in a range of about 0.01 wt. % to about 2 wt. %, based on the weight of the sorbent. Sulfur is the most preferred Group VIA element. Where desired, the hydrocracking suppressor is incorporated either at the same time as the sorbent metal or sequentially, also using conventional techniques, such as impregnation.

If desired, presulfiding may be accomplished by exposing the virgin sorbent to a sulfur source under liquid or gas phase conditions. Sulfur levels in the presulfided product are from about 0.01 to about 1.0 wt. %, preferably from about 0.02 to about 0.7 wt. %, most preferably from about 0.02 to about 0.5 wt. %. Alternately, sulfur is incorporated by exposing the sorbent, preferably a virgin sorbent, to a dilute aqueous solution of from about 1 to about 10% sulfuric acid under impregnation conditions.

Regeneration of the metal sorbent is facilitated by including an agent that catalyzes the oxidation or reduction reaction required to restore the sulfur sorbent to its initial, active condition. This period of regeneration can be reduced by at least about 30%, more preferably at least about 50%. Such agents include, but are not necessarily limited to the noble metals of Group VIII of the Periodic Table of the Elements, preferably at least one of Ir, Pt, Pd, and Rh. The addition of from about 0.01 wt. % to about 10 wt. % of at least one of these metals benefits regenerability of the sorbent by decreasing, for example, the regeneration period and decreasing the regeneration temperature. Of course, if the metal(s) of the sorbent are only noble metal(s) then no additional noble metal needs to be added. Co—Ni bimetallic sorbents typically experience more complete regeneration than the corresponding Ni only sorbent.

Regeneration of the sorbent by first treating it with an oxidizing atmosphere may require the initial displacement of combustible organics. These combustible organics are displaced by suitable inert gases including but not necessarily limited to nitrogen, carbon dioxide, carbon monoxide, and helium. Thereafter, the spent sorbent is exposed to an oxidizing atmosphere under conditions effective to oxidize the metal sulfide bound to the sorbent to a metal sulfite or sulfate and ultimately to a metal oxide. Typical oxidation temperatures range from about 200° C. to about 850° C., preferably from about 300° C. to about 600° C., most preferably from about 325° C. to about 500° C. The oxidation process is operable over a range of temperatures and pressures consistent with the intended objectives in terms of product quality improvement and consistent with any downstream process with which this invention is combined in either a common or sequential reactor assembly. Operating pressure may be from about 0 to about 3,000 psig, preferably about 50 to about 1000 psig, at air flow rates of from about 10 to about 2,000 standard cubic feet per hour per pound (SCF/hr/lb) of sorbent, preferably about 20 to about 1500 SCF/hr/lb of sorbent, and more preferably about 100 to about 1000 SCF/hr/lb of sorbent.

Suitable oxidizing gases are oxygen, and oxygen blends which may also include one or more diluents such as steam, carbon dioxide, and inerts such as nitrogen and helium. It is preferred that the oxidizing gas be sulfur free, or substantially sulfur free, the latter being achievable by conventional technologies currently in use. The oxidizing gas generally contains from about 1% to about 50% oxygen, preferably from about 5% to about 30% oxygen, and more preferably from about 10% to about 20% oxygen, with any remainder being inerts.

The spent sorbent, after first being exposed to an oxidizing atmosphere and optional inert purge, is then exposed to a reducing atmosphere. The reducing atmosphere conditions are effective to reduce the sorbent to a state that is active for the absorption of hydrogen sulfide. Typical reducing atmosphere temperatures range from about 100° C. to about 700° C., preferably from about 250° C. to about 600° C., and most preferably from about 275° C. to about 550° C. The reduction process is operable over a range of temperatures and pressures consistent with the intended objective of restoring at least a portion of the sorbent's $H_2S$ absorbtion capacity for re-use in either a common or sequential reactor assembly. Operating pressure may be from about 0 to about 3000 psig, preferably about 50 to about 1000 psig, at $H_2$ gas rates of from about 10 to about 2,000 SCF/hr/lb of sorbent, preferably about 20 to about 1500 SCF/hr/lb of sorbent, and more preferably about 100 to about 1000 SCF/hr/lb of sorbent.

Hydrogen may be, and preferably is, present in the reducing atmosphere and may be supplied pure or admixed with other passive or inert gases as is frequently the case in a refining or chemical processing environment. It is preferred that the hydrogen stream be sulfur free, or essentially sulfur free, the latter being achievable by conventional technologies. The regeneration stream contains from about 50% to about 100% hydrogen, preferably from about 70 to about 100% hydrogen, and more preferably from about 80 to about 100% hydrogen, with any remainder being inerts or saturated light hydrocarbon gases.

Properties desired in a regenerable hydrogen sulfide sorbent include, for example, capacity to absorb hydrogen sulfide, regenerability, and the retention of both qualities over multicycle adsorption-regeneration sequences. Although it is preferred that both capacity and regenerability for a given sorbent approach about 100%, it is understood that this level is not a requirement for an effective regenerable sorbent. A capacity and regenerability that allow a frequency of regeneration that is reasonable and compatible with the overall process objective are acceptable and adequate. With this qualification in mind, an "effective regenerated capacity" is from about 5% to about 100% of a first cycle capacity, preferably from about 10% to about 100% of a first cycle capacity, most preferably from about 20% to about 100% of a first cycle capacity. A "first cycle capacity" refers to the sorbent capacity of a fresh or "virgin" sorbent material.

In a preferred embodiment, the sorbent is used in conjunction with distillate and naphtha hydrodesulftirization (HDS) processes, preferably one of the processes described in U.S. Pat. Nos. 5,925,239, 5,928,498, and 5,935,420, all incorporated herein by reference. Typical hydrodesulfurization conditions include temperatures from about 40° C. to about 500° C. (104–930° F.), preferably about 200° C. to about 450° C. (390–840° F.), and more preferably about 225° C. to about 400° C. (437–750° F.). Operating pressures include about 50 to about 3000 psig, preferably 50 to about 1200 psig, and more preferably about 100 to about 800 psig at gas rates of about 50 to about 10,000 SCF/B, preferably about 100 to about 7500 SCF/B, and more preferably about 500 to about 5000 SCF/B. The liquid hourly space velocity may be varied over the range of about 0.1 to about I 00 V/V/Hr, preferably about 0.3 to about 40 V/V/Hr, and more preferably about 0.5 to about 30 V/V/Hr. The liquid hourly space velocity is based on the volume of feed per volume of catalyst per hour, i.e., V/V/Hr.

Various sorbent bed configurations may be used in the practice of the present invention. Examples of suitable bed configurations include, but are not necessarily limited to bubbling beds, fixed beds operated in a cocurrent or countercurrent mode, non-fluidized moving beds, fluidized beds, or a slurry of HDS catalyst and sorbent in a continuously stirred tank reactor ("CSTR"), or slurry bubble column. Fluidized beds may be advantageous in conjunction with processes where continuous regeneration of the sorbent is needed. In addition, flow-through, fluidized bed technology which includes a disengaging zone for catalyst and sorbent may be useful to regenerate sorbent particles. The process can operate under liquid phase, vapor phase or mixed phase conditions. It should be noted that the HDS catalyst and the sorbent may be separate particles, a composite of HDS catalyst and sorbent, and an HDS catalyst impregnated onto a sorbent. However, when the sorbent and HDS catalyst are arranged so that the HDS catalyst is present during sorbent reduction, undesirable desulfiding of the HDS catalyst may result. In such cases, it may be desirable to adjust the sorbent reduction conditions to abate the affects of HDS catalyst desulfurization, or to subject the HDS catalyst to a re-sulfiding step prior to re-use, or to employ an HDS catalyst that does not require sulfiding, such as a noble metal HDS catalyst. Alternately, the HDS catalyst may be re-sulfided when it is exposed to the sulfur-containing hydrocarbon feed.

Fixed bed configurations may be operated in either of cocurrent and countercurrent modes, i.e., with hydrogen-containing treat gas flowing over the HDS catalyst in the same or opposite direction as the sulfur-containing feed. In another embodiment, the hydrogen-containing treat gas is employed in a "once-through" arrangement and is therefore not recycled. Countercurrent HDS arrangements may be preferred in cases where increased contacting between the sulfur-containing feed, the treat gas, and the HDS catalyst would be desired and in cases where increased $H_2S$ stripping would be beneficial.

Those skilled in the art are aware that the choice of bed configuration for an HDS catalyst and a hydrogen sulfide sorbent depends upon the objective of the overall process, particularly when the process is integrated with one or more subsequent processes, or when the objective of the overall process is to favor the selectivity of one aspect of product quality relative to another. However, it should be noted that preferably the sorbent is not placed upstream of the HDS catalyst.

A preferred embodiment uses a stacked bed configuration with a swing reactor designed to permit regeneration of spent sorbent while a fresh sorbent is placed in service. In a stacked bed configuration, the HDS catalyst is stacked, or layered, above and upstream of the sorbent. The stacked beds either may occupy a common reactor, or the HDS catalyst may occupy a separate reactor upstream of the reactor containing the sorbent. This dedicated reactor sequence is preferred when the HDS catalyst and the sorbent require different reactor temperatures.

In another embodiment, the sorbent and the HDS catalyst are used in a mixed bed configuration. In this configuration, particles of the HDS catalyst are intimately intermixed with those of the sorbent. In both the stacked bed and the mixed bed configurations, the two components—that is, the HDS catalyst and the sorbent—may share similar or identical shapes and sizes, or the particles of one component may differ, for example, in shape, density, and/or size from the particles of the second component. The use of particles having different sizes may be employed when, for example, a simple physical separation of the bed components is desired upon discharge or reworking.

In yet another embodiment, the two components are blended together to form a composite particle incorporating both the HDS catalyst and the sorbent. For example, a finely divided, powdered Pt on alumina HDS catalyst is uniformly blended with a regenerable sorbent and the mixture is formed into a common catalyst particle. Or, the regenerable sorbent may be incorporated into the support, and Pt, for example, may be impregnated onto the sorbent containing support, such as alumina.

In another two component configuration, an alumina support is impregnated with an HDS metal or metals and a sorbent on a common base. Both metals may be distributed uniformly throughout the catalyst particle, or the sorbent and/or HDS components may be deposited preferentially on the outside of the particle to produce a rim, or eggshell, sorbent or HDS rich zone.

In a preferred embodiment, a ZnO sorbent is combined with an Fe, Co, Ni, Mo, or W catalyst, a noble metal catalyst, or combinations thereof. The catalyst and sorbent can be blended together to form a composite particle or the catalyst may be supported on the ZnO sorbent. The ZnO sorbent may be supported on an inorganic support material in order to increase, for example, surface area, pore volume, pore diameter, strength and/or attrition resistance.

A three component bed configuration also may be used. In one embodiment, denoted as mixed/stacked, a mixed HDS catalyst/sorbent bed is configured upstream of a single HDS/hydrogenation catalyst. In another embodiment, known as a stacked/stacked/stacked configuration, the three components are layered from top to bottom as follows: HDS catalyst/sorbent/HDS catalyst. In one embodiment, three component systems may occupy a common reactor. In another embodiment, a three component system may be used in a two-reactor train in which the HDS catalyst/sorbent occupy a lead reactor in a mixed or stacked configuration and the HDS catalyst occupies the tail reactor. This arrangement allows for the operation of two reactor sections at different process conditions, especially temperature, and imparts flexibility in controlling process parameters such as selectivity and product quality.

The composition of the bed is independent of configuration and may be varied in accordance with the specific or integrated process to which the invention is applied. If the capacity of the sorbent is limiting, the composition of the bed must be consistent with the expected lifetime, or cycle, of the process. These parameters are in turn sensitive to the sorbent content of the feed being processed and to the degree of desulfurization desired. For these reasons, the composition of the bed is flexible and variable, and the optimal bed composition for one application may not serve an alternative application equally well. In general, the weight ratio of the sorbent to the hydrodesulfurization catalyst may range from about 0.01 to about 1000, preferably from about 0.5 to about 40, and more preferably from about 0.7 to about 30. For three component configurations, the ranges cited apply to the mixed zone of the mixed/stacked arrangement and to the first two zones of the stacked/stacked/stacked design. The hydrodesulfurization catalyst present in the final zone of these two arrays is generally present at a weight ratio that is equal to or less than the combined weight compositions of the upstream zones.

The process may be used as a stand-alone process for, e.g., purposes of various fuels, lubes, and chemicals applications. Alternately, the process may be combined and integrated with other processes in a manner so that the net process affords product and process advantages and improvements relative to the individual processes not combined. The following embodiments are included to illustrate, but not limit, uses for the process of this invention.

Processes relating to fuels processes include: desulfurization of gasoline range feed and product streams; desulfurization of distillate streams; desulfurization of FCC streams preceding recycle to $2^{nd}$ stage process; desulfurization of hydrocracking feeds; multi-ring aromatic conversion through selective ring opening; aromatics saturation processes; hydroisomerization; sulfur removal from natural, synthesis, and recycle gas streams and from field condensate streams. Processes relating to the manufacture of lubricants include: hydrocracking, product quality improvement through mild finishing treatment; optimization of white oil processes by decreasing catalyst investment and/or extending service factor. Processes relating to chemical processing include: substitute for environmentally unfriendly nickel based hydroprocesses; preparation of high quality feedstocks for olefin manufacture through various cracking processes and for the production of oxygenates by oxyfunctionalization processes; production of solvent and polymer grade olefins and aromatics.

This invention is illustrated by, but not limited to, the following examples, in which the following experimental conditions were used unless otherwise indicated.

GENERAL CONDITIONS

The capacity and regenerability of the hydrogen sulfide sorbents were assessed using a Cahn TG 121 Thermogravimetric Analyzer using nominally equivalent weight charges of each sorbent. The candidate sorbents were initially calcined in air at 400° C. for 3 hr prior to being placed in the analyzer. The sorbent was heated at 500° C. for 1 hr in hydrogen and then cooled to 325° C. and exposed to a gas blend containing 1000 ppm $H_2S$ in $H_2$ for a period of 2 hr during which interval the weight gain associated with the adsorption of $H_2S$ was recorded. The spent sorbent subsequently was heated to varying temperatures and exposed to flowing air to oxidize the sulfide to sulfate. The oxidized sorbent was then exposed to $H_2$ for one hour at or below 500° C. during which interval the desorption of $H_2S$, or the regeneration of the sorbent, was noted. In multicycle testing this sequence was duplicated as noted to simulate repetitive adsorption-regeneration cycles.

The sorbents were prepared by incipient wetness impregnation of the various support materials with aqueous solutions of the metal nitrates. The extrudates were air dried under vacuum at 120° C. for 24 hr. Calcination in flowing air was carried out in a small catalyst pretreat unit or in a thernogravimetric unit dedicated to this function. In both cases the calcination was conducted at 400° C. for 3 hr. All sorbent compositions in the examples are nominal wt. % metal on support.

EXAMPLE I

The decomposition temperatures of several metal sulfates in hydrogen were measured in the TGA apparatus. The results appear in the following table:

| Metal Sulfate | Decomposition Temperature, ° C. |
|---|---|
| $CuSO_4$ | 185 |
| $NiSO_4$ | 335 |
| $CoSO_4$ | 420 |
| $FeSO_4$ | 440 |
| $MnSO_4$ | >500 |

These temperatures indicate that the oxidation of a metal sulfide to its corresponding sulfate followed by reduction will restore an active form of the metal for the reconversion to the metal sulfide by reaction with hydrogen sulfide. With the exception of Mn, hydrogen sulfide sorbents based on the metals listed above are regenerable by and oxidation-reduction sequence using temperatures at or below 500° C.

EXAMPLE II

A 20% $Cu/ZrO_2$ sorbent was exposed to $H_2S$ in $H_2$ as described in Example I. The sorbent experienced a weight gain of 4.01%. The spent sorbent was heated in flowing air at 100 ml/min at 325° C. for about 1 hour followed by reduction in flowing hydrogen at 100 ml/min at 325° C. The regenerated $Cu/ZrO_2$ was tested in a second cycle service and experienced a weight gain of 3.62 wt. % indicating a regeneration efficiency of the sorbent of about 90%.

EXAMPLE III

The procedure in Example II was repeated using a 10% $Co/SiO_2$ sorbent. The regeneration conditions of Example II failed to reactivate the sorbent.

EXAMPLE IV

The sorbent in Example III was exposed to flowing air at 100 ml/min at 500° C. for about 1 hour followed by reduction in flowing hydrogen at 100 ml/min at 500° C. The sorbent was regenerated to about 100% capacity.

EXAMPLE V

The procedure in Example IV was repeated using a $Fe/ZrO_2$ sorbent. The weight gain in the initial cycle was 5.6 wt. %. The spent sorbent was regenerated as in Example IV at 450° C. The weight gain in the second cycle was 4.2 wt. % yielding a regeneration efficiency of 74%.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

What is claimed is:

1. A process for regenerating a hydrogen sulfide sorbent comprising:

providing a spent hydrogen sulfide sorbent containing an effective quantity of a sorbent metal or metal oxide wherein the metal is at least one of Fe, Ni, Cu, Co, and Zn, said hydrogen sulfide sorbent having a level of sulfur defining a first cycle capacity for absorbing hydrogen sulfide provided that when the metal is Cu, it is a cracking suppressor in an amount ranging from 2 to about 6 wt %; and exposing said spent hydrogen sulfide sorbent to an oxidizing atmosphere under conditions effective to oxidize said spent hydrogen sulfide sorbent; and removing sulfur from a reducing stream in order to form a substantially sulfur-free reducing stream;

reducing said oxidized hydrogen sulfide sorbent to the substantially sulfur-free reducing stream for a regenerating time period under conditions effective for said reducing stream to reduce and regenerate said spent hydrogen sulfide sorbent.

2. The process of claim 1 wherein said reducing atmosphere is provided by a hydrogen-containing gas.

3. The process of claim 1 wherein said oxidizing conditions include a temperature from about 200° C. to about 850° C. and said reducing conditions include a temperature from about 100° C. to about 700° C.

4. The process of claim 3 wherein said oxidizing conditions include a temperature from about 300° C. to about 600° C. and said reducing conditions include a temperature from about 250° C. to about 600° C.

5. The process of claim 1 wherein said spent hydrogen sulfide sorbent comprises a regeneration rate enhancing amount of a noble metal selected from Group VIII of the Period Table of the elements, and wherein said regeneration rate enhancing amount reduces the period of regeneration by at least about 30%.

6. The process of claim 5 wherein the regeneration rate enhancing amount ranges from about 0.01 wt. % to about 10 wt. %, based on the weight of the hydrogen sulfide sorbent.

7. The process of claim 5 wherein said regeneration rate enhancing amount reduces said regenerated period by at least about 50%.

8. The process of claim 1 wherein said sorbent metal exhibits a level of hydrocracking activity, and said process further comprises incorporating into said hydrogen sulfide sorbent a hydrocracking suppressing quantity of at least one hydrocracking suppressor selected from one or more of Group IB, Group IVA, and Group VIA of the Periodic Table.

9. The process of claim 8 wherein the hydrocracking suppressor is
   (i) at least one of Cu, Ag, Au, Sn, and Pb, and the suppressing quantity ranges from about 1 wt. % to about 10 wt. %, or
   (ii) at least one Group VIA element, and the suppressing quantity ranges from about 0.01 wt. % to about 2 wt. %.

10. The process of claim 9 wherein the sorbent metal is zinc and at least a portion of the zinc is present as zinc oxide.

11. The process of claim 1 wherein the sorbent is supported on a refractory inorganic oxide.

12. The process of claim 1 further comprising exposing said hydrogen sulfide sorbent to an inert or non-reactive purge following the oxidizing atmosphere exposure and before the reducing atmosphere exposure.

13. A desulfurization process, comprising:
   (a) contacting hydrocarbon stream containing sulfur with a catalytically effective amount of a catalyst system under catalytic hydrodesulfurization conditions, the catalyst system being comprised of:
      (i) a hydrodesulfurization catalyst containing at least one of Mo, W, Fe, Co, Ni, Pt, Pd, Ir, and Rh; and,
      (ii) a hydrogen sulfide sorbent containing at least one metal or oxide of the metal, the metal(s) being selected from Fe, Ni, Co, and Cu, said hydrogen sulfide sorbent having a level of sulfur defining a first cycle capacity for absorbing hydrogen sulfide, said contacting producing a desulfurized product and a spent hydrogen sulfide sorbent; and then
   (b) exposing said spent hydrogen sulfide sorbent to an oxidizing atmosphere under conditions effective to oxidize said spent hydrogen sulfide sorbent; and then
   (c) reducing said oxidized hydrogen sulfide sorbent to a substantially sulfur-free reducing stream under conditions effective for said reducing stream to reduce and regenerate said spent hydrogen sulfide sorbent, thereby producing a regenerated sorbent.

14. The process of claim 13 wherein said reducing atmosphere is provided by a hydrogen-containing gas.

15. The process of claim 13 wherein said oxidizing conditions include a temperature from about 200° C. to about 850° C. and said reducing conditions include a temperature from about 100° C. to about 700° C.

16. The process of claim 15 wherein said oxidizing conditions include a temperature from about 300° C. to about 600° C. and said reducing conditions include a temperature from about 250° C. to about 600° C.

17. The process of claim 13 wherein said spent hydrogen sulfide sorbent comprises a regeneration rate enhancing amount of a noble metal selected from Group VIII of the Period Table of the elements, and wherein said regeneration reducing amount shortens said regenerating period by at least about 30%.

18. The process of claim 17 wherein said regeneration rate enhancing amount reduces said regenerating period by at least about 50%.

19. The process of claim 17 wherein the regeneration rate enhancing amount ranges from about 0.01 wt. % to about 10 wt. %, based on the weight of the hydrogen sulfide sorbent.

20. The process of claim 13 wherein the sorbent further comprises at least one hydrocracking suppressor selected from Group IB, Group IVA, and Group VIA of the Periodic Table in a suppressing quantity sufficient to suppress hydrocracking.

21. The process of claim 20 wherein the hydrocracking suppressor is
   (i) at least one of Cu, Ag, Au, Sn, and Pb, and the suppressing quantity ranges from about 1 wt. % to about 10 wt. %, or
   (ii) at least one Group VIA element, and the suppressing quantity ranges from about 0.01 wt. % to about 2 wt. %.

22. The process of claim 13 wherein the hydrogen sulfide sorbent is the regenerated sorbent.

23. The process of claim 22 wherein steps (a), (b), and (c) are performed continuously.

24. The process of claim 13 wherein at least one of the hydrodesulfurization catalyst and the hydrogen sulfide sorbent is supported on an inorganic refractory support.

25. The process of claim 13 wherein the weight ratio of the hydrogen sulfide sorbent to the hydrodesulfurization catalyst ranges from about 0.01 to about 1000.

26. The process of claim 25 wherein the hydrodesulfurization catalyst and the hydrogen sulfide sorbent are in the form of separate particles.

27. The process of claim 25 wherein the hydrodesulfurization catalyst and the hydrogen sulfide sorbent are in the form of a composited particle.

28. The process of claim 25 wherein the catalyst system is in the form of catalyst particles, and wherein the hydrogen sulfide sorbent is impregnated with the hydrodesulfurization catalyst.

29. The process of claim 13 wherein the hydrogen sulfide sorbent contains ZnO and wherein the hydrodesulfurization catalyst contains at least one of Fe, Co, Ni, Mo, and W.

30. The process of claim 13 operated in at least one of a moving bed, a bubbling bed, a non-fluidized moving bed, a fluidized bed, a continuously stirred tank reactor, and a slurry bubble column.

31. The process of claim 30 wherein the process is a fixed bed process operated in one of
   (i) cocurrent and
   (ii) countercurrent mode,
and wherein the catalytic hydrodesulfurization conditions include a temperature of about 40° C. to about 500° C., a pressure ranging from about 100 psig to about 3,000 psig, a treat gas rate ranging from about 50 to about 10,000 SCF/B, and a space velocity ranging from about 0.1 to about 100 V/V/Hr.

* * * * *